(12) United States Patent
Weldon et al.

(10) Patent No.: US 8,496,911 B2
(45) Date of Patent: Jul. 30, 2013

(54) TISSUE STABILIZATION FOR HEART FAILURE

(75) Inventors: Norman R. Weldon, Amelia Island, FL (US); Matthew F. Ogle, Fitchburg, WI (US)

(73) Assignee: Vatrix CHF, Inc., Maple Grove, MN (US)

( * ) Notice: Subject to any disclaimer, the term of this patent is extended or adjusted under 35 U.S.C. 154(b) by 326 days.

(21) Appl. No.: 12/845,414

(22) Filed: Jul. 28, 2010

(65) Prior Publication Data
US 2011/0081423 A1 Apr. 7, 2011

Related U.S. Application Data

(60) Provisional application No. 61/229,335, filed on Jul. 29, 2009.

(51) Int. Cl.
*A61K 49/00* (2006.01)
(52) U.S. Cl.
USPC .......................................... 424/9.1; 424/9.2
(58) Field of Classification Search
USPC ........................................................ 424/9.1
See application file for complete search history.

(56) References Cited

U.S. PATENT DOCUMENTS

| | | | |
|---|---|---|---|
| 2,987,446 A | 6/1961 | Riethmüller | |
| 5,081,157 A | 1/1992 | Pomerantz | |
| 5,147,514 A | 9/1992 | Mechanic | |
| 5,252,344 A | 10/1993 | Shi | |
| 5,332,475 A | 7/1994 | Mechanic | |
| 5,391,156 A | 2/1995 | Hildwein et al. | |
| 5,415,631 A | 5/1995 | Churinetz et al. | |
| 5,512,291 A | 4/1996 | Li | |
| 5,702,343 A | 12/1997 | Alferness | |
| 5,750,150 A | 5/1998 | Okazaki et al. | |
| 5,834,449 A | 11/1998 | Thompson et al. | |
| 5,880,242 A | 3/1999 | Hu et al. | |
| 5,955,097 A | 9/1999 | Tapolsky et al. | |
| 5,980,455 A | 11/1999 | Daniel et al. | |
| 6,063,770 A | 5/2000 | Falcon | |
| 6,071,541 A | 6/2000 | Murad | |
| 6,228,387 B1 | 5/2001 | Borod | |
| 6,258,122 B1 | 7/2001 | Tweden et al. | |
| 6,290,949 B1 | 9/2001 | French et al. | |
| 6,391,538 B1 | 5/2002 | Vyavahare et al. | |
| 6,437,004 B1 | 8/2002 | Perricone | |
| 6,471,723 B1 | 10/2002 | Ashworth et al. | |
| 6,494,896 B1 | 12/2002 | D'Alessio et al. | |
| 6,773,704 B1 | 8/2004 | Chapman et al. | |
| 7,213,601 B2 | 5/2007 | Stevens et al. | |
| 7,252,834 B2 | 8/2007 | Vyavahare et al. | |
| 7,371,257 B2 | 5/2008 | Sahatjian et al. | |
| 7,422,588 B2 | 9/2008 | Mulier et al. | |
| 7,713,543 B2 | 5/2010 | Vyavahare et al. | |
| 2003/0130746 A1 | 7/2003 | Ashworth et al. | |
| 2003/0170287 A1 | 9/2003 | Prescott | |
| 2003/0171287 A1 | 9/2003 | Morishita et al. | |
| 2003/0232895 A1 | 12/2003 | Omidian et al. | |
| 2004/0153145 A1 | 8/2004 | Simionescu et al. | |
| 2004/0191215 A1 | 9/2004 | Froix et al. | |
| 2006/0034925 A1 | 2/2006 | Au et al. | |
| 2006/0159641 A1 | 7/2006 | Girardot et al. | |
| 2006/0240066 A1 | 10/2006 | Vyavahare et al. | |
| 2007/0128289 A1 | 6/2007 | Zhao | |
| 2007/0281026 A1 | 12/2007 | Vyavahare et al. | |
| 2007/0282422 A1 | 12/2007 | Biggs et al. | |
| 2008/0319185 A1 | 12/2008 | Himmeldirk et al. | |
| 2009/0022772 A1 | 1/2009 | Carpenter et al. | |
| 2009/0155337 A1 | 6/2009 | Schreck et al. | |
| 2009/0214654 A1 | 8/2009 | Isenburg et al. | |
| 2010/0119605 A1 | 5/2010 | Isenburg et al. | |

FOREIGN PATENT DOCUMENTS

| | | |
|---|---|---|
| EP | 0617964 A1 | 10/1994 |
| GB | 2057437 A | 4/1981 |
| JP | 10-130155 | 5/1998 |
| WO | 2004/047620 A2 | 6/2004 |
| WO | 2007/064152 A1 | 6/2007 |

OTHER PUBLICATIONS

Wetzel et al. "Lipolysis and fatty acid transport in rat heart: electron microscopic study" Am J Physiol., 1984, 246(5 Pt 1):C467-C485.*
Chung et al. "Thermo-sensitive and biodegradable hydrogels based on stereocoplexed Pluronic multi-block copolymers for controlled protein delivery", J of Controlled Release, 2008, 127:22-30.*
Barbetakis et al. "Cardiac temponade secondary to metastasis from adenocarcinoma of the parotid gland" World J of Surgical Oncology, 2003, 1:20:1-4.*
Adams et al., "Crossiink formation in porcine valves stabilized by dye-mediated photooxidation," J Biomed Mater Res 57(4): 582-587 (2001).
Ben-Horin et al., "The composition of normal pericardial fluid and its implications for diagnosing pericardial effusions," Am J Med. 118(6):636-40 (2005) (Abstract only).
Bigi et al., "Stabilization of gelatin films by crosslinking with genipin," Biomaterials 23:4827-4832 (2002).
Broderick et al., "Anatomic pitfalls of the heart and pericardium," RadioGraphics 25:441-453 (2005).
Connolly et al., "Triglycidylamine crosslinking of porcine aortic valve cusps or bovine pericardium results in improved biocompatibility, biomechanics, and calcification resistance," Am J Pathol 166(1): 1-13 (2005).
Harvard Health Publications, "Hemorrhoids and what to do about them," http://www.revolutionhealth.com/conditions/digestive/hemorrhoids/introduction/what-to-do, Aug. 21, 2006.

(Continued)

*Primary Examiner* — Bin Shen
(74) *Attorney, Agent, or Firm* — Dardi & Herbert, PLLC; Peter S. Dardi

(57) ABSTRACT

Methods and devices for the stabilization of heart tissue to treat congestive heart failure using a therapeutic composition are discussed. The therapeutic composition can comprise an elastin stabilization agent, a collagen stabilization agent, or a combination thereof and be applied to the pericardium, to the outer surface of the myocardium, or a combination thereof using a catheter type of device with an attached reservoir. Controlled placement and release of the therapeutic composition can be achieved using a delivery vehicle to formulate the composition.

16 Claims, 4 Drawing Sheets

OTHER PUBLICATIONS

Isenburg et al., "Elastin stabilization for treatment of abdominal aortic aneurysms," Circulation 115:1729-1737 (2007).

Isenburg et al., "Tannic acid treatment enhances biostabllity and reduces calcification of glutaraldehyde fixed aortic wall," Biomaterials 26:1237-1245 (2005).

Jöbsis et al., "The visceral pericardium: macromolecular structure and contribution to passive mechanical properties of the left ventricle," Am J Physiol Heart Circ Physiol 293:H3379-H3387(2007).

Kasyanov et al., "Tannic acid mimicking dendrimers as small intestine submucosa stabilizing nanomordants," Biomaterials 27:745-751 (2006).

Kobayashi et al., "Comparison of elastolytic activity between experimental aneurysm and experimental diabetes mellitus," Biol. Pharm. Bull. 21(7):775-777 (1998).

Meuris et al., "Porcine stentless bioprostheses: Prevention of aortic wall calcification by dye-mediated photo-oxidation," Artificial Organs 27(6): 537-543 (2003).

Mourelo et al., "Surgical instrumentation perspective: Use of bovine pericardium in partial gastric resection: Report of a case," Bariatric Times 3(4):1-13 (2006).

Osakabe et al., "Quantitative change of elastin, fibrillin and collagen in abdominal aortic aneurysm." Nippon Ronen Igakkai Zasshi (Japanese Journal of Geriatrics) 37(12):979-983 (2000) (See English language abstract on p. 983).

Petite et al., "Cytocompatibility of calf pericardium treated by glutaraldehyde and by the acyl azide methods in an organotypic culture model," Biomaterials 16(13): 1003-1008 (1995).

Ross, Jr., "Acute Displacement of the diastolic pressure-volume curve of left ventricle: Role of the pericardium and the right ventricle," Circulation 59:32-37 (1979).

Sacks et al., "Collagen fiber architecture of bovine pericardium," ASAIO J. 40(3):M632-637 (1994) (Abstract only).

Yamaguchi et al., "The time course of elastin fiber degeneration in a rat aneurysm model," Surgery Today 30:727-731 (2000).

\* cited by examiner

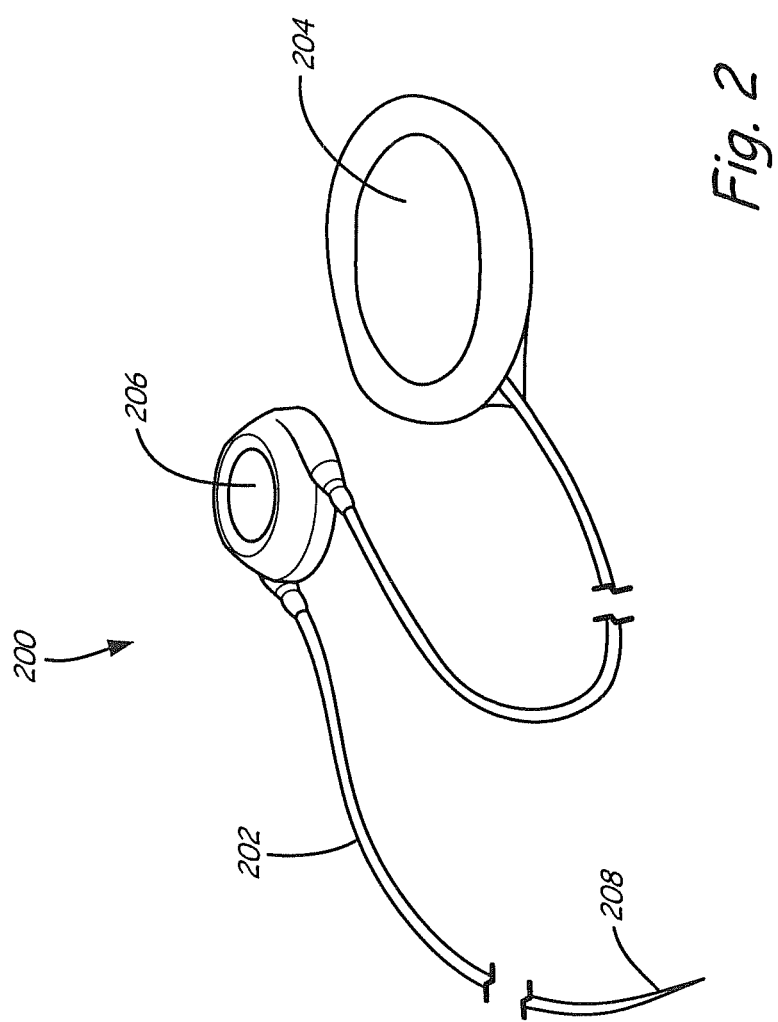

TISSUE STABILIZATION FOR HEART FAILURE

CROSS REFERENCE TO RELATED APPLICATIONS

This application claims priority to U.S. provisional patent application Ser. No. 61/229,335, filed on Jul. 29, 2009 to Weldon et al., entitled "Tissue Stabilization for Heart Failure," incorporated herein by reference.

FIELD OF THE INVENTION

The inventions, in general, are related to stabilization of heart tissue, such as pericardium tissue, for the treatment of congestive heart failure or the like. The inventions are further related to compositions, methods, and devices useful for heart tissue stabilization.

BACKGROUND

Congestive heart failure (CHF) or heart failure is a condition in which the heart can not pump enough blood to the body's other organs and tissues. This pumping deficiency can result, for example, from one or more of the following instances: (a) narrowed arteries that supply blood to the heart muscle such as those in coronary artery disease; (b) past heart attack, or myocardial infarction, with scar tissue in the heart muscle that interferes with the heart muscle's normal work; (c) high blood pressure; (d) heart valve disease such as those due to past rheumatic fever or other causes; (e) primary disease of the heart muscle itself, called cardiomyopathy; (f) heart defects present at birth such as those from congenital heart defects; and (g) infection of the heart valves and/or heart muscle itself such as those from endocarditis and/or myocarditis.

The "failing" or weakened heart keeps working but not as efficiently as it should. People with heart failure generally have difficulty exerting themselves because they become short of breath and tired. As blood flow from the heart slows as a result of heart failure, blood returning to the heart through the veins backs up, causing congestion in the tissues drained by the veins. Often swelling, i.e., edema results from the back up of fluid in the veins. Most often the swelling is observed in the legs and ankles, but swelling can happen in other parts of the body, too. Sometimes fluid collects in the lungs and interferes with breathing, causing shortness of breath, especially when a person is lying down. Heart failure also can affect the kidneys' ability to dispose of sodium and water. The retained water increases the edema.

There are potentially a variety of causes of congestive heart failure, and certain of these causes may be more directly treatable than others. For example, if the heart failure is caused by an abnormal heart valve, the valve can be surgically replaced. Generally, if the heart becomes so damaged that it can't be repaired, a more drastic approach may be considered. For cases with more severe damage to the heart, a heart transplant can be an option. Most people with mild and moderate congestive heart failure can be treated, and proper medical supervision may prevent the patients from becoming invalids.

SUMMARY OF THE INVENTION

In a first aspect, the invention pertains to a method for the stabilization of heart tissue. The method comprises the step of applying a therapeutic composition to the pericardium, to the outer surface of the myocardium, or a combination thereof. The therapeutic composition comprises an elastin stabilization agent, a collagen stabilization agent, or a combination thereof. The therapeutic composition further comprises a delivery vehicle that comprises precursor of a hydrogel, polymer nanoparticles with the therapeutic composition embedded therein, or a combination thereof. In some embodiments, the precursor of hydrogel comprises Pluronic block copolymers. In some embodiments the nanoparticles comprises poly (lactic acid-co-glycolic) acid. The elastin stabilization agent and the collagen stabilization agent can be applied simultaneously or sequentially.

In some embodiments, the therapeutic composition is applied through the access of the heart using a catheter structure. In some embodiments, the therapeutic composition is applied through the access of the heart using an access port or alike. In some embodiment, the therapeutic composition is applied to the heart tissue using a cardiac reinforcement wrap or a patch. The method can comprise an additional aspiration step before the application of the therapeutic composition. The application of the therapeutic composition can be repeated with the same or a different therapeutic composition.

The elastin stabilization agent used in the method can comprise a compound that is tannic acid or a derivative thereof, a flavonoid or a flavonoid derivative, a flavolignan or a flavolignan derivative, a phenolic rhizome or a phenolic rhizome derivative, a flavan-3-ol or a flavan-3-ol derivative, an ellagic acid or an ellagic acid derivative, a procyanidin or a procyanidin derivative, anthocyanins, quercetin, (+)-catechin, (−)-epicatechin, pentagalloylglucose, nobotanin, epigallocatechin gallate, gallotannins, an extract of olive oil or a derivative of an extract of olive oil, cocoa bean or a derivative of a cocoa bean, *Camellia* or a derivative of *camellia*, licorice or a derivative of licorice, sea whip or a derivative of sea whip, aloe vera or a derivative of aloe vera, chamomile or a derivative of chamomile, a combination thereof, or a pharmaceutically acceptable salt thereof. In additional or alternative embodiments, the elastin stabilization agent can comprise pentagalloylglucose, an analog of pentagalloylglucose, a pharmaceutically acceptable salt thereof, or a combination thereof. The collagen stabilization agent used in the method can comprise an aldehyde with at least two aldehyde groups, a polyamine with carbodiimide, a photo-catalytic dye, genipin, an epoxide, an azide ester, or a combination thereof In one embodiment, the collagen stabilization agent comprises glutaraldehyde. In some embodiments, the therapeutic composition comprises a photo-activated crosslinking agent.

In another aspect, the invention pertains to a medical device for the stabilization of heart tissue. The device comprises a catheter and a reservoir that comprises a therapeutic composition. The reservoir and the catheter are in fluid communication with each other. The catheter is configured to access the heart tissue from the exterior of the chest. The therapeutic composition comprises an elastin stabilization agent, a collagen stabilization agent, or a combination thereof. In some embodiments, the catheter comprises a one way or directional shield to protect coronary arteries. In other embodiments, the catheter comprises a tapered tip portion. In further embodiments, the catheter comprises a needle-like tip portion. In additional embodiments, the device further comprises an applicator that is configured to extend through the catheter to deliver the therapeutic composition.

BRIEF DESCRIPTION OF THE DRAWINGS

FIG. 2 is a schematic diagram of a delivery device using a catheter.

DETAILED DESCRIPTION OF PREFERRED EMBODIMENTS

Figure 1:
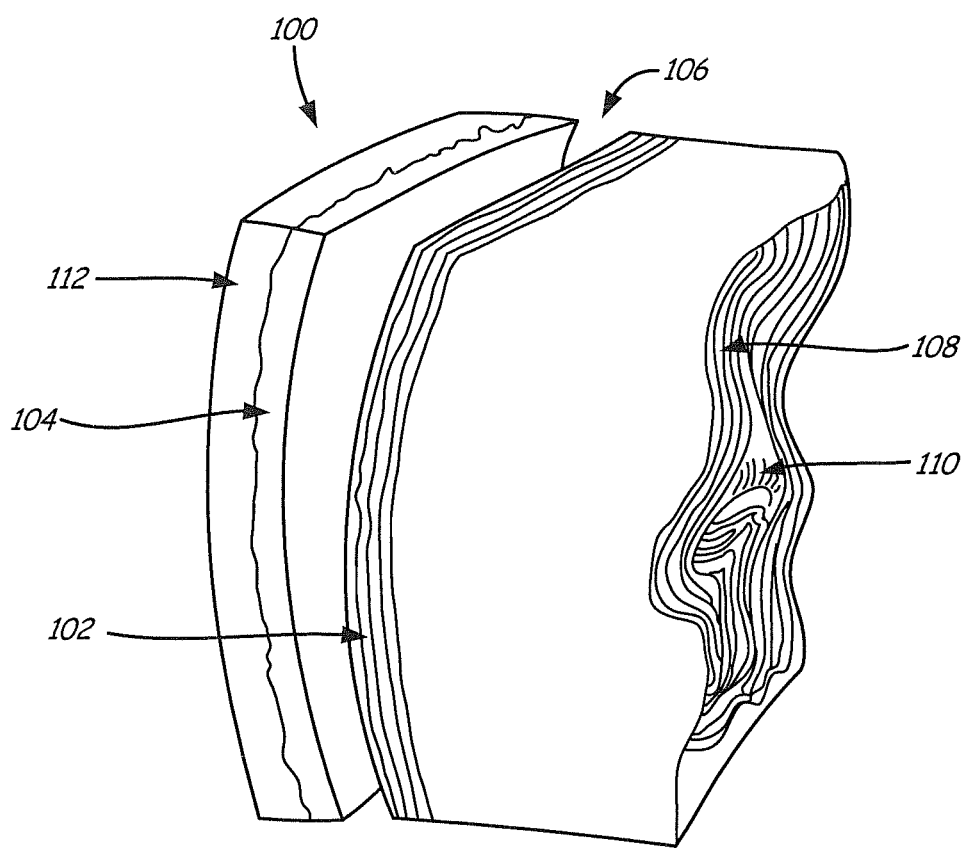
FIG. 1 is a schematic diagram of different layers of pericardium in relation to the heart muscle.

As described herein, congestive heart failure can be addressed through the stabilization of the heart muscle and/or associated tissue, e.g. the pericardium, using a stabilization composition. Congestive heart failure in many instances can be associated with an expansion of the heart due to the mechanical weakening of the heart muscle. The present approach provides for the strengthening of tissue associated with heart, such as pericardium, using appropriately formulated tissue crosslinkers. The strengthened pericardium in turn facilitates the heart muscle to pump more effectively. The present approach thus provides treatment of congestive heart failure generally under conditions that do not significantly damage the heart muscle cells. In addition to pericardium, other heart tissue may be similarly strengthened or stabilized to impart positive facilitative function to the pumping action of the heart. In some embodiments, a stabilization fluid can be applied directly to the pericardium surrounding the heart and/or to the myocardium surface. In general, the tissues for stabilization can be accessed using less invasive techniques through the chest into the thoracic cavity. Suitable devices can be used to deliver the stabilization compositions. Alternatively, the tissue stabilization composition can be incorporated into or delivered through a cardiac wrap or alike. In some embodiment, the cardiac wrap may comprise bovine pericardium tissue. The term "stabilization composition" is generally used interchangeably herein with the term "therapeutic composition".

In patients with congestive heart failure, the heart is not pumping sufficiently to provide desired levels of blood circulation. Therefore, it is desirable to help these patients to increase the pumping efficiency of the heart. The pumping efficiency can be improved through the stiffening of the environment of the heart such that the available pumping forces can be more effectively directed to the movement of blood. Thus, as described herein, the stabilization composition can mechanically strengthen the outer surface of the heart muscle and/or the tissue surrounding the heart muscle. In general, patients of particular interest are human patients, although the treatments described herein can be applied to other mammalian patients, such as farm animals, porcine, bovine or horses, as well as pets, such as dogs or cats.

Specifically, the stabilization composition can be applied, for example, to the patient's pericardium, heart muscle, e.g., myocardium, or a combination thereof. A study has presented evidence that the mechanical properties of the pericardium can directly influence the corresponding pumping function of the heart muscle. See Jöbsis et al., "The visceral pericardium: macromolecular structure and contribution to passive mechanical properties of the left ventricle," Am. J. Physiology-Heart and Circulation Physiology, 293:H3379-H3387 (October 2007) and Ross Jr., "Acute Displacement of the Diastolic Pressure-Volume Curve of the Left Ventricle: Role of the Pericardium and the Right Ventricle," Circulation, 59:32-37 (1979), both of which are incorporated herein by reference. Due to the role of the pericardium in heart function, a patient's pericardium can be treated with a stabilization composition to improve heart function with a decreased risk of damage to the heart muscle. Similarly, treatment of the pericardium can be combined with a mild treatment of the myocardium. Suitable variations of these treatments can be used as appropriate. The stabilization compositions described herein can provide mechanical stabilization to the heart muscle and/or associated tissue, such as pericardium, which is collectively referred to as heart tissue hereinafter.

The heart tissue generally is comprised of structural proteins including, for example, elastin and collagen within an extracellular matrix. Crosslinking of the structural proteins can change the mechanical properties of the heart tissue, which can result in an increase in mechanical strength while providing pliable tissue. The conditions for applying the stabilization compositions can be selected to reduce the toxicity to the heart muscle cells. The stabilization compositions can comprise an elastin crosslinking agent, such as PGG, a collagen crosslinking agent, such as glutaraldehyde, or a combination thereof. In some embodiments, a photoactivated crosslinking agent can be used. Detailed discussion of formulations and compositions for connective tissue stabilization generally through the use of crosslinking agents are disclosed in U.S. Pat. No. 7,713,543 (the '543 patent) to Vyavahare et al., entitled "Elastin Stabilization of Connective Tissue", U.S. Patent Application Publication No. 20100119605 (the '605 Application) to Isenburg et al., entitled "Compositions for Tissue Stabilization", and U.S. Patent Application Publication No. 20090214654 (the '654 Application) to Isenburg et al., entitled "Treatment of Aneurysm with Application of Connective Tissue Stabilization Agent in Combination with a Delivery Vehicle," all incorporated herein by reference. In some embodiments in which both an elastin stabilization agent and a collagen stabilization agent are applied, the elastin stabilization/crosslinking agent and the collagen stabilization/crosslinking agent can be administered sequentially or simultaneously.

The myocardium or heart muscle comprises some collagen and elastin structural proteins. These fibrous proteins form the basis for stabilization of the heart muscle. The pericardium generally is derived from connective tissue, and the pericardium has a significant amount of collagen and elastin. Due to the high content of collagen and elastin in the pericardial tissue, the pericardial tissue can be significantly influenced by the stabilization compounds described herein. Thus, the pericardial tissue can be made stiffer through the application of the stabilization compounds described herein. As illustrated in FIG. 1, the pericardium 100 comprises two layers: visceral pericardium 102 and parietal pericardium 104 and a pericardial cavity 106 between the two layers. The visceral pericardium layer is closely apposed to the heart muscle, also referred to as myocardium 108, while the fibrous parietal pericardium layer provides a more rigid outer shell to the pericardial cavity. The myocardium 108 surrounds endocardium 110. A fibrous layer 112 is attached to the exterior of the parietal pericardium 102. The pericardial cavity contains pericardial fluid, which has a normal volume of roughly 50 mL for an adult human patient.

In some embodiments, the treatment compositions described herein can be directly administered into the pericardial cavity using an injection or the like to make the surrounding layers of the pericardium stiffer. In other embodiments, the therapeutic composition can be administered to a portion of the fibrous layer of the parietal pericardium, which involves less disruption of the pericardium structure. In some embodiments, the therapeutic composition can be administered to a portion of the surface of myocardium. In other embodiments, the therapeutic composition can be administered to a portion of the visceral pericardium, which may also affect the myocardium due to the close relationship of these tissues. When at least a portion of the pericardium and/or myocardium is stabilized with the therapeutic composition, the pericardium and/or myocardium can experience a stiffer environment that correspondingly influences function of the heart. Consequently, the left ventricular pressure is expected to correspondingly increase during heart pumping based on the mechanical interaction between the heart muscle and the pericardium. If the left ventricular pressure can be increased, it is expected that heart function correspondingly improves in circumstances in which the heart is initially experiencing heart failure.

The therapeutic or stabilization compositions for the in vivo heart tissue stabilization described herein can comprise delivery vehicles formulated to impart a controlled placement of the active ingredients onto or into the heart tissue. In some embodiments, the active ingredients may be formulated with the delivery vehicle to form a liquid therapeutic composition. In some embodiments, upon application of the liquid therapeutic composition to the heart tissue in vivo, the liquid composition hardens or gels to form a non-flowing material that can affix to the heart tissue. The active ingredients contained in the therapeutic composition, i.e. the elastin crosslinker and/or the collagen crosslinker, may subsequently release from the affixed material in a controlled manner to stabilize the heart tissue. In embodiments where photo-activated crosslinkers are used, an appropriate delivery vehicle may be formulated into the therapeutic composition to facilitate the photo catalysis process. The therapeutic composition may be applied directly to heart muscle and/or to the tissue surrounding the heart such as pericardium. Depending on the targeted tissue that the therapeutic composition is applied, the therapeutic compositions may be formulated accordingly to suit the particular characteristics of each specific targeted tissue. For example, when the therapeutic composition is administered directly to the pericardial cavity, the composition should not significantly interfere with the normal lubricating function of the pericardial fluid.

In general, less-invasive devices and methods for accessing the heart tissue, such as those known in the art, may be employed or adapted for the application of the therapeutic compositions to the targeted heart tissue described herein. Suitable less invasive devices generally can comprise a catheter or the like, and a reservoir to supply the therapeutic composition through the catheter as well as an appropriate control component. The catheter or the like can be introduced through a small incision such that the distal end of the catheter can be directed to a selected delivery location. The reservoir can comprise one or more quantities of composition for delivery through the catheter, and the device generally is designed for controlled delivery of fluid from the reservoir through the catheter. The device can be designed to mix components of the therapeutic composition at the time of delivery, for example, to avoid premature solidification or gelling. Direct application of the therapeutic compositions to the pericardium may be particularly advantageous in some applications due to the positive impact of heart function imparted and a small amount interference with the viability of the heart muscle as well as reducing risk of injury to the heart muscle or to blood vessels supplying the heart muscle.

Based on the efficacy of the tissue crosslinking stabilization agents optionally combined with advantages available with a delivery vehicle to control placement of the therapeutic composition and the less-invasive devices to facilitate delivery, the heart tissue stabilization approaches disclosed herein provide an advantageous treatment option for heart failure. The approaches disclosed herein can have the advantage of incurring little interference to the health of the heart while providing the potential for significant improvement of proper function of the heart. The heart tissue stabilization approaches disclosed herein can be applied multiple times with the same or different active therapeutic compositions at the same or different time intervals to provide desired therapeutic as well as prophylactic effects to the patient. The heart tissue stabilization approaches may additionally combined with other interventional approaches such as using medication or mechanical stabilization to treat heart failure.

Medication used to treat congestive heart failure can perform one or more of a set of different functions. Angiotensin converting enzyme (ACE) inhibitors and vasodilators expand blood vessels and decrease resistance to blood flow. An expansion of blood vessels allows blood to flow more easily and makes the heart's work easier or more efficient. Beta blockers, i.e. beta-adrenergic blocking agents can improve how well the heart's left lower chamber (left ventricle) pumps. Digitalis increases the pumping action of the heart, while diuretics help the body eliminate excess salt and water. If high blood pressure is associated with the heart failure, blood pressure medicine can help treat the heart failure. The stabilization approaches described herein can be used in addition to or as an alternative to drug treatments.

Mechanical stabilization of heart tissues have been proposed involving surgical interventions. Examples of proposed mechanical stabilization approaches are described in U.S. Pat. No. 7,213,601 to Stevens et al. (the '601 patent), entitled "Minimally-invasive Devices and Methods for Treatment of Congestive Heart Failure" and U.S. Pat. No. 5,702,343 (the '343 patent) to Alferness entitled "Cardiac Reinforcement Device," both of which are incorporated herein by reference. As described in the '343 patent, a reinforcing jacket is placed around the heart. The '601 patent describes the surgical removal of heart tissue to reduce the size of the heart chamber. The approaches for tissue stabilization described herein provide an alternative or an additional treatment approach to other mechanical stabilization approaches. The procedure described herein can be advantageous since the natural heart structure can be stabilized to improve heart function with less disruption of the natural heart function.

Elastin Stabilization

As described in U.S. Pat. No. 7,713,543 (the '543 patent) to Vyavahare et al., entitled "Elastin Stabilization of Connective Tissue", tissue with an elastin component can be strengthened with a phenolic compound. In particular, it is believed that any of a number of natural and synthetic phenolic compounds can bind elastin and thereby strengthen the elastin containing tissue, such as connective tissue. In some embodiments, elastin binding phenolic compounds include, for example, any compound that comprises at least one phenolic hydroxyl group bound to a hydrophobic core. While not wishing to be bound by theory, it is believed that interaction between the phenolic compound and elastin proteins have aspects involving both the hydroxyl group as well as the hydrophobic core of the molecules. In particular, the large hydrophobic regions of the elastin protein, which are believed to contain sites susceptible to elastase-mediated cleavage, are believed to contain sites of association between the hydrophobic core of the phenolic compound and the protein. Thus, the association of the hydrophobic core of the phenolic stabilization compound with the hydrophobic region of the elastin may contribute to inhibition of elastin cleavage by elastase. In certain embodiments, the phenolic compounds can comprise one or more double bonds, with which the phenolic compounds can covalently bind to the elastin, forming an even stronger protective association between the phenolic compound and the elastin containing tissue.

Suitable phenolic compounds with one or more phenolic hydroxyl groups extending from the hydrophobic core of the molecule can include, but are not limited to, flavonoids and their derivatives e.g., anthocyanins, quercetin, flavolignans, phenolic rhizomes, flavan-3-ols e.g. (+)-catechin and (−)-epicatechin, other tannins and derivatives thereof e.g. tannic acid, pentagalloylglucose, nobotanin, epigallocatechin gallate, and gallotannins, ellagic acid, procyanidins, and the like. Suitable phenolic compounds include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaiinic*, extracts of licorice, sea whip, aloe vera, chamomile, and the like.

In some embodiments, the phenolic compounds can be tannins and derivatives thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

Pentagalloylglucose (PGG) and tannic acid (TA) are members of the tannin family, a group of naturally derived polyphenolic compounds. PGG is a structurally similar but less toxic compound relative to tannic acid. PGG is naturally occurring, relatively non-toxic and not expected to exhibit significant side effects. PGG is characterized by a D-glucose molecule esterified at all five hydroxyl moieties by gallic acid (3,4,5-trihydroxybenzoic acid). In general, it is understood that the PGG molecule can have 1-4 galloyl group(s) and the galloyl groups can assume different stereo chemical forms. For example, PGG can be in either alpha or beta forms. The '543 patent reported that periarterial treatment with PGG preserves elastin fiber integrity and hinders aneurysmal dilatation of the abdominal aorta in a clinically relevant model of aortic aneurysms. Analogs of PGG may also be used as elastin stabilizers. Methods of making analogs of PGG are discussed in U.S. Patent Application Publication No. 2008/0319185 to Himmeldirk et al., entitled "Efficient method to synthesize benzyl group-protected alpha-pentagalloylglucose (alpha-PGG) and its analogues", incorporated herein by reference, which can be adapted to produce analogs of PGG for the usage discussed herein.

For compositions that are expected to impart a fast and strong binding thus stabilization effect, relatively high concentration of elastin stabilization agents maybe used. Toxicity reduction in these relatively high concentration cases is especially important. For example, when tannin family of compounds such as PGG or TA is used, it can be desirable to maintain low level of free or unbound gallic acid in the composition. In some embodiments, the composition can include little or no unbound gallic acid. In one embodiment, the composition can include less than about 5% un-bound gallic acid. In one embodiment, the composition can include between about 1% and about 5% unbound gallic acid. In one embodiment, the composition can include less than about 1% unbound gallic acid.

In general, a therapeutic composition for stabilizing heart tissue can comprise one or more buffers as are generally known in the art. For example, a composition comprising one or more phenolic compounds and having a pH from about 4.0 to about 9.0 may be formulated with inclusion of a biocompatible buffer such as distilled water, saline, phosphate buffers, borate buffers, HEPES, PIPES, and MOPSO. In one embodiment, a stabilization composition may be formulated to have a pH of between about 5.5 and about 7.4. A person of ordinary skill in the art will recognize that additional ranges of pH within the explicit ranges herein are contemplated and are within the present disclosure. In general, the stabilization composition can comprise an elastin stabilization compound and/or a collagen stabilization compound.

In general, the phenolic compounds described herein can be provided as a biocompatible composition. For instance, compositions disclosed herein can include one or more phenolic compounds in a concentration that can vary over a wide range, with a suitable concentration generally depending on the particular application, the delivery site targeted by the phenolic compound and the mode of delivery. For example, in one embodiment, a composition can comprise one or more phenolic compounds at a concentration from about 0.0001% to about 10%. A person of ordinary skill in the art will recognize that additional concentration ranges within the explicit ranges herein are contemplated and are within the present disclosure. Unless otherwise noted, all concentrations reported herein are weight/volume percentages. Mass to volume percentage is the relationship of a solute to a solvent expressed as grams of solute per milliliter of the total solution, as used herein and as standard in the particular art. For example, 0.06 g of pentagalloylglucose (PGG) in 100 mL of solution is considered a 0.06% w/v PGG solution.

It should be noted, however, that while these exemplary concentrations are effective in certain embodiments, the invention encompasses compositions comprising a wider range of phenolic compound concentrations. For example, actual concentrations used may be influenced by the organ targeted by the procedure, size of the targeted area, desired incubation time, and preferred pH, in addition to delivery mode, as mentioned above. In some embodiments, the disclosed compositions can have concentrations of a phenolic compound ranging from about 0.1% to about 1%.

Suitable delivery vehicles can be formulated with the phenolic compounds described herein to impart desired properties, such as viscosity upon application, which are discussed further below.

Collagen Stabilization

Additionally, collagen crosslinking/stabilization compositions have been found to provide a high degree of stabilization of connective tissues, as described in U.S. Patent Application Publication No. 20100119605 (the '605 Application) to Isenburg et al., entitled "Compositions for Tissue Stabilization". In some embodiments, a collagen crosslinking/stabilization agent can be used as a sole therapeutic compound to stabilize collagen in the connective tissue such as pericardium. In other embodiments, a collagen crosslinking/stabilization agent can be effectively combined with an elastin stabilizing agent. The combination of treatment agents can be contacted with the tissue simultaneously or sequentially.

Multi-functional reagents, such as glutaraldehyde, diamine, genipin, acyl azide, and epoxyamine, are known to cross-link functional groups in collagen and thereby tissue having a collagen component. Some known functional groups for collagen cross-linking are amino, thiol, hydroxyl, and carbonyl in collagen and/or nearby proteins. By binding to and crosslinking collagen and/or nearby proteins, the multi-functional agents can increase the mechanical strength of the tissue. Collagen containing tissue treated with collagen crosslinking/stabilization agent with or without combination with elastin stabilization agent may exhibit enhanced mechanical property, resistance to enzymatic degradation such as elastase and collagenase, and high thermal denaturation temperature. In the case of cardiac tissues, the increased mechanical strength of the heart tissue can correspondingly increase the pumping function of the weakened heart.

Glutaraldehyde and other multi-functional aldehyde compounds are known to bind to and stabilize collagen in a collagen containing tissue. Glutaraldehyde in particular self-polymerizes to form polymer chains that are believed to be effective at crosslinking between collagen fibers. Glutaraldehyde polymerizes with itself and/or with nearby active groups from collagen and/or other proteins creating crosslinks in the treated tissue. The chemical crosslinks in the tissue can contribute to increased mechanical strength of the treated tissue. However, residual unreacted free aldehyde groups from glutaraldehyde can contribute with regards to toxicity and calcification. Methods to reduce toxicity from unreacted free aldehyde known in the art can be adapted for use in the in vivo heart tissue stabilization composition and method described herein. For example, treatment of bioprosthetic tissue to reduce glutaraldehyde toxicity is described in U.S. Pat. No. 6,471,723 to Ashworth et al., entitled "Biocompatible Prosthetic Tissue," incorporated herein by reference.

Difunctional aldehydes, e.g., glutaraldehyde, have been used for some time to fix collagenous tissue, such as bovine pericardium, for the preparation of bioprosthetic materials, but alternative collagen crosslinking agents have been proposed. One of the alternative collagen stabilizing agents comprises diamines, generally with at least two free primary amine groups, such as 1,6-hexanediamine and 1,7-heptanediamine. The diamines bond to carboxyl groups in proteins to form a crosslinked structure. It has been found that coupling agents and coupling enhancers facilitate this crosslinking/stabilization process with diamines. For example, suitable coupling agents include carbodiimides, such as 1-ethyl-3-(3-dimethyl aminopropyl)-carbodiimide (EDC) and/or N-hydroxysuccinimide (NHS). The carbodiimides function as a coupling agent in the crosslinking/stabilization reaction, and are generally used along with a coupling enhancer. For example, EDC can be used in conjunction with N-hydroxysulfosuccinimide (Sulfo-NHS), which acts as an enhancer to the reaction. Other suitable coupling enhancers include, for example, N-hydroxybenzotriazole (HOBt), N,N-dimethyl-4-aminopyridine (DMAP) and N-hydroxysuccinimide. By coupling the amine and carboxyl groups within the tissue, this treatment creates amide bonds or bridges between and/or inside proteins, thus crosslinking the tissue. In vitro crosslinking of bioprosthetic tissue with diamines along with coupling agents and/or coupling enhancers is described further for example in published U.S. patent application 2006/0159641A to Girardot et al., entitled "Variably Crosslinked Tissue," incorporated herein by reference.

Collagen stabilization can be achieved using other active agent or alternative methods. For example, collagen stabilization in tissue can be triggered by a light sensitive dye, similar to the PhotoFix™ technology used by Carbomedics for bioprosthetic heart valves; genipin is a naturally occurring plant compound capable of crosslinking collagen; epoxy compounds have reactive functional groups that are reactive with several functional groups found in proteins, such epoxies can be used to crosslink proteins, especially collagen, within tissue. Additionally, epoxy amine polymer compounds are also suitable collagen crosslinking agents that are described further in U.S. Pat. No. 6,391,538 to Vyavahare et al., entitled "Stabilization of Implantable Bioprosthetic Tissue," incorporated herein by reference. An example of a poly-epoxyamine compound suitable as a collagen crosslinking agent is triglycidylamine, a triepoxy amine. The use of triglycidyleamine in stabilization of bovine pericardium tissue described in Connolly et al. Am J. Pathol. 2005, 166 (1): 1-13 entitled "Triglycidylamine crosslinking of porcine aortic valve cusps or bovine pericardium results in improved biocompatibility, biomechanics, and calcification resistance," incorporated herein by reference, can similarly be adapted for the use in the in vivo stabilization of heart tissue. Moreover, free carboxyl groups on collagen can be converted into acyl azide groups, which react with free amino groups on adjacent side chains to crosslink the collagen tissue. This crosslinking approach is described in Petite et al. *Biomaterials* 1995; 16(13): 1003-1008, incorporated herein by reference.

Photoactivated crosslinking agents may be particularly desirable as in vivo collagen stabilization agents for the in vivo stabilization of heart tissue, since greater control can be applied to the crosslinking process. For example, the use of a photoactivated process provides for greater control of the crosslinking reaction since migration of chemicals from the delivery location does not result in crosslinking unless photoactivated. Photoactivated crosslinking is also referred to as photo-oxidation fixation, which can be based on the use of photoactive dye as catalyst called photocatalyst. Suitable photocatalyst include, for example, PhotoFix™ used by Carbomedics for bioprosthetic heart valves, methylene blue, methylene green, rose bengal, riboflavin, proflavin, fluorescein, eosin, pyridoxal-5-phosphate, or combinations thereof. The photocatalyst aids in the conversion of amino acids within the tissue, subsequently allowing for crosslink formation between the converted amino acid and nearby amino acids, thus stabilize the tissue.

Photoactivated crosslinking for in vitro stabilization of prosthetic tissue are well known in the art and can be adapted for use in the in vivo heart tissue stabilization described herein. Examples of porcine heart valve stabilization using photo-oxidation fixation methods are disclosed in the following articles: Adams A K, Taman E A, Campbell L, et al. *J Biomed Mater Res* 2001; 57 (4): 582-587 and Meuris B, Phillips R, Moore M A, et al. *Artif Organs* 2003; 27 (6): 537-543), both of which are incorporated by reference. Methods for ex vivo cross-linking collagen with a photocatalyst are described further in U.S. Pat. No. 5,147,514 to Mechanic et al, entitled "Process for cross-linking collagenous material and resulting product," incorporated herein by reference, can similarly be adapted for the in vivo stabilization of heart tissue. Photoactivated collagen stabilization requires exposure of the dye treated tissue to a light source. In the case of in vivo heart tissue stabilization, such light source can be supplied by for example, through optical fiber using an access port. Additionally, oxygen, which may be supplied to the therapeutic collagen stabilization composition to facilitate the completion of the photo-oxidative reaction, can be supplied with a catheter type of device.

In general, tissue stabilization agents can comprise an elastin stabilization agent and/or a collagen stabilization agent, which maybe used for effective in vivo treatment of heart tissue employing an appropriate delivery device. Agents may have acute in vivo toxicity such that control of the treatment conditions and isolation of the treatment site during the delivery and treatment process can be advantageous. Specifically, glutaraldehyde can be relatively toxic to living cells, and other collagen crosslinking agents and elastin crosslinking agents can be somewhat toxic. In particular, glutaraldehyde has been used to fix tissue to remove antigens and form an inert matrix for prosthetic implantation, for example, as bioprosthetic heart valves. Complete fixation of tissue with glutaraldehyde generally kills all cells in the tissue. Through the selection of the composition of the stabilization solution and the control of the treatment conditions, which is discussed further below, the viability of the tissue can be substantially maintained while improving the mechanical stability of the tissue.

In general, the therapeutic composition can comprise one or more buffers as are generally known in the art. For example, a composition comprising one or more collagen crosslinking/stabilization agent and having a pH from about 4.0 to about 9.0 may be formulated with inclusion of a biocompatible buffer such as distilled water, saline, phosphate buffers, borate buffers, HEPES, PIPES, and MOPSO. In some embodiments, a composition of the invention may be formulated to have a pH of between about 5.5 and about 7.4. A person of ordinary skill in the art will recognize that additional ranges of pH within the explicit ranges above are contemplated and are within the present disclosure.

In general, the one or more collagen crosslinking/stabilization agent with or without elastin crosslinking/stabilization agent described herein can be provided as a biocompatible composition. For instance, compositions disclosed herein can comprise one or more collagen crosslinking/stabilization agent in a concentration that can extend over a wide range, with a selected concentration generally depending on the particular application, the delivery site targeted by the one or more collagen crosslinking/stabilization agent and the mode for the delivery process. For example, in one embodiment, a composition of the invention can comprise one or more collagen crosslinking/stabilization agent at a concentration from about 0.0001% to about 10%. It should be noted, however, that while these exemplary concentrations are effective in certain embodiments, the invention encompasses compositions comprising a wider range of collagen crosslinking/stabilization agent concentrations. For example, actual concentrations used may be influenced by the organ targeted by the procedure, size of the targeted area, desired incubation time, and preferred pH, in addition to delivery mode, as mentioned above. In one embodiment, the disclosed compositions can have concentrations of one or more collagen crosslinking/stabilization agent ranging from about 0.1% to about 1%. A person of ordinary skill in the art will recognize that additional ranges of concentration within the explicit ranges above are contemplated and are within the present disclosure.

Suitable delivery vehicles can be formulated with the one or more collagen crosslinking/stabilization agent described herein to impart desired properties, such as viscosity upon application, which are discussed further below.

Delivery Vehicle

The choice of delivery vehicle used for the therapeutic in vivo heart tissue stabilization composition described herein can be particularly significant to impart a controlled placement and release of the stabilization composition. In some embodiments, the delivery vehicle, for example, may be formulated with the stabilization composition to form a liquid treatment composition. Upon application of the liquid treatment composition to the heart tissue in vivo, the liquid composition can harden or gel to form a viscous material that attaches to the heart tissue. The attachment of the gelled or hardened liquid therapeutic composition to the heart tissue can reduce or eliminate undesirable contact of the therapeutic composition to tissues surrounding the heart that is not intended to be subjected to stabilization. The active ingredients, i.e. the collagen stabilization composition can subsequently release from the hardened viscous material in a controlled manner to stabilize the heart tissue. The elastin stabilization/crosslinking agent alone, the collagen stabilization/crosslinking agent alone, or a composition containing both the elastin and collagen stabilization/crosslinking agents can be formulated with specific delivery vehicle to impart the desired therapeutic effect. In some embodiments, a delivery vehicle can be used as disclosed in the U.S. Patent Application Publication No. 20090214654 (the '654 Application) to Isenburg et al., entitled "Treatment of Aneurysm with Application of Connective Tissue Stabilization Agent in Combination with a Delivery Vehicle".

In some embodiments, the therapeutic formulations described herein comprise one or more tissue stabilization agents combined with a delivery vehicle. The tissue stabilization agent can be elastin stabilization/crosslinking agent, collagen stabilization crosslinking agent or a combination thereof. The delivery vehicle can be a hydrogel polymer. A hydrogel polymer can provide for the gradual release of the stabilization agent as well as a more controlled delivery of the agent to the heart tissue. In particular, delivery vehicles such as a Pluronic™ hydrogel can provide controlled release of one or more heart tissue stabilization agents to heart to improve the efficacy of the stabilization agents and provide for desirable delivery approaches. The therapeutic compositions formed by the combination of the stabilization agents with the delivery vehicles can be directly delivered to all parts of the pericardium. Based on the site of administration, the therapeutic compositions used can be formulated accordingly to suite different tissues.

In one embodiment, the hydrogel of the delivery vehicle comprises penta-galloylglucose in a gel form. In some embodiments, the hydrogel comprises Pluronic™ hydrogel. In some embodiments, the hydrogel is loaded with penta-galloylglucose, glutaraldehyde, or a combination thereof. In additional embodiments, the hydrogel comprises Pluronic™ F-127 hydrogel. The therapeutic composition can also comprise gallic acid scavenger, a lipid lowering medication, an anti-bacterial agent, an anti-fungal agent, or a combination thereof. In some embodiments, the delivery vehicle comprises precursor of the hydrogel and the stabilization agent. In one embodiment, the delivery vehicle comprises a solution of Pluronic™ block copolymers with penta-galloylglucose, glutaraldehyde, or a combination thereof. In some embodiments, the therapeutic composition further comprises pharmaceutically acceptable carriers and/or excipients.

In some embodiments, the therapeutic compositions can comprise one or more delivery vehicles combined with one or more stabilization agent that is effective to stabilize heart tissue in congestive heart failure. The delivery vehicles can be selected to provide a sustained release of the stabilization agent(s) as well as to control the conditions of the contact between the stabilization agent and the tissue. Suitable delivery vehicles can include, for example, a gel formed from a stabilization agent, a hydrogel composition, or combinations thereof In some embodiments, the therapeutic compositions can be administered on multiple occasions to achieve the desire therapeutic effect. The length of the period between each administration can be determined by the combination of the specific release profile of the therapeutic composition used and the condition of the heart tissue in congestive heart failure. Throughout the treatment periods, diagnostic methods can be employed to monitor the condition of the heart.

The delivery vehicles can provide for both control of placement of the therapeutic compositions as well as for the controlled release of the therapeutic composition. The controlled release disclosed herein is alternatively referred to as sustained release, which refers to delivery of the stabilization agent in vivo over a period of time following administration. The control of the placement of the therapeutic composition can be accomplished through the solidification of the delivery vehicle upon deliver in vivo. For example, upon contact of the tissue, the delivery vehicle can gel and stay localized, thus preventing undesired migration of the active ingredients significantly beyond targeted tissue for treatment. If desired, controlled localization of the therapeutic composition can be monitored through methods known in the art such as spiking the composition with fluorescent dye followed by imaging method.

In some embodiments, the controlled release can be, for example, less than about a week or alternatively can be less than four days. However, it is also contemplated that the controlled release can be for periods longer than one week using the composition. In some embodiment the release period can be no more than about 1 hour, 2, hours, 4 hours, 8 hours, 12 hours, 24 hours, 48 hours, 72 hours, 96 hours, or a combination thereof. In some other embodiment, the release period is at least about 5 weeks, 10 weeks, 15 weeks, 20 weeks, 25 weeks, 30 weeks, 35 weeks, 40 weeks, 45 weeks, 50 weeks or 55 weeks. A person of ordinary skill in the art will recognize that additional ranges of time within these explicit ranges are contemplated and are within the present disclosure.

In some embodiments, a hydrogel is formed in vivo from a precursor of the hydrogel, such as block copolymers that crosslink when a threshold temperature such as human physiological temperature is reached. The hydrogel formed does not dissolve in aqueous solution generally as a result of crosslinking if the temperature remains about the same or higher. The block copolymers used can be soluble at lower temperature such as room temperature. Because of the thermo-gelation properties of the block copolymers, tissue stabilization agent can be combined with an appropriate amount of the block copolymers to form a therapeutic composition solution. The therapeutic composition when administered to the heart tissue in a patient, forms a hydrogel in situ that stay localized to provide sustained release of the tissue stabilization agent. The physico-chemical effect of the tissue stabilization agent on the resulting gel formulation are taken into consideration by investigating the effect of variables such as pH, gelation temperature, solubility, water content, and viscoelasticity. The hydrogel can be biodegradable. For these embodiments, the release profile of the biodegradable hydrogel is additionally affected by the biodegradation of the hydrogel itself. In some embodiments, the tissue stabilization agents are additionally embedded in polymers to form nanoparticles before forming a dispersion with the precursors of hydrogel.

One of the commercially available block copolymers for hydrogels are Pluronic™ polymers that generally comprise polyoxy-propylene/polyoxy-ethylene or polyoxy-ethylene/polyoxy-propylene/polyoxy-ethylene block copolymers. Hydrogels from the crosslinking of these block copolymers and similar compositions can be referred to as Pluronic™ hydrogels. The resultant hydrogel is additionally biodegradable. Gel forming polymers like poloxamer 407 are in situ gellable hydrogels and are of interest as delivery vehicles since they provide soft, permeable, and hydrophilic interfaces with body tissues. They are also listed in US, European pharmacopoeia and FDA's inactive ingredient database. Poloxamer 407 has been evaluated for its toxicity potential and is acceptable for use as a vehicle to achieve drug delivery. The block copolymers used for the gelation directly affect the gelation temperature and other significant properties of the final hydrogel, for example, the rate in which an active agent is release from the hydrogel.

In general, the final concentration of the polymer in the final therapeutic composition can be in the range of about 5% to about 98% by weight, and the concentration of tissue stabilization agent in the therapeutic composition can be in the range of about 0.05 to about 100 mg/mL. Additionally, the hydrogel can be in the range of 5-95%, 7-80%, 8-75%, 9-70%, 10-60%, 12-50%, or 15-40% by weight, and the tissue stabilization agent can have concentration that is in the range of about 0.05-100 mg/mL, 0.1-95 mg/mL, 0.2-90 mg/mL, 0.5-80 mg/mL, 1.0-70 mg/mL, 2.0-60 mg/mL, 5-50 mg/mL, or 10-40 mg/mL in the hydrogel precursor solution, as well as corresponding groups of ranges with these particular end points. In some embodiments, the tissue stabilization agent is PGG that has a concentration in the range of about 0.1-50 mg/mL in the hydrogel precursor solution. In one embodiment, the concentration of the PGG is in the range of about 0.1-2 mg/mL. A person of ordinary skill in the art will recognize that additional ranges of concentrations within these explicit ranges are contemplated and are within the present disclosure.

Polymeric particles for drug delivery generally include, for example, biocompatible polymers and may or may not be spherical. The polymeric particles generally can have an average particle diameter of no more than about 5 microns, in further embodiments no more than a micron and in additional embodiments no more than about 250 nanometers, where the diameter is an average dimension through the particle center for non-spherical particles. The delivery of drugs using nanoparticles and microparticles is described further for example in published U.S. Patent application 2006/0034925 to Au et al, entitled "Tumor Targeting Drug-Loaded Particles," incorporated herein by reference.

In general, it can be advantageous to form the nanoparticles from a bioresorbable polymer binder since the gradual dissolution of the polymer binder can facilitate release of the stabilization agent from the particles. Any suitable biocompatible bioresorbable polymer generally can be used. Suitable bioresorbable polymers include, for example, dextran, hydroxyethyl starch, gelatin, polyvinylpyrolidone and combinations thereof In further embodiments, suitable bioresorbable polymers comprise polyhydroxy acids and copolymers thereof, such as poly(caprolactone), poly(dimethyl glycolic acid) or poly (hydroxy butyrate) as well as polymers and copolymers of lactic acid and/or glycolic acid. The formation of nanoparticles from poly(lactic-co-glycolic acid (PLGA) is generally known in the art.

For prolonged tissue stabilization agent delivery, other controlled release delivery vehicle (such as nanoparticles) can be entrapped within hydrogels without any detrimental effects. The incorporation of nanoparticles, besides providing good control of the release of the encapsulated stabilization agent, can have additional advantages, such as provide isolation of the drug, especially when two or more active ingredients are used, slower release rates, improved residence times, and achievement of different release profiles. Although nanoparticles alone can be used to achieve long term drug release of weeks to months, such vehicles typically do not result in constant release profiles. Nanoparticles can exhibit an initial rapid burst release as a result of surface associated stabilization agent. Moreover, localization of nanoparticles to the site can be difficult. Particles, such as nanoparticles, embedded within hydrogels can provide synergistic delivery effects because the hydrogel matrix prevents stabilization agent degradation, allows localized delivery, and also allows additional control over the release kinetics of the stabilization agent.

The loading of nanoparticles within a hydrogel can be adjusted to achieve a desired amount of tissue stabilizing agent to the patient. In some embodiments, the nanoparticles comprise an elastin stabilization agent combined with the particle forming polymer. In some other embodiments, the nanoparticles comprise a collagen stabilization agent combined with the particle forming polymer. In yet some other embodiments, the nanoparticles comprise a combination of a collagen stabilization agent and an elastin stabilization agent. In some other embodiments, some nanoparticles comprise one or more collagen stabilization agent and the other nanoparticles comprise one or more elastin stabilization agent. In some embodiments, the nanoparticles can be in the range of about 0.5-95, 1.0-90, 2.0-80, 2.5-70, 5-60, 7-50, 10-40 or 20-30 weight percent in the hydrogel. A person of ordinary skill in the art will recognize that additional ranges of nanoparticle loading within a hydrogel-based therapeutic composition are contemplated and are within the present disclosure. Specifically, for example, PGG-PLGA nanoparticles can be prepared by emulsion solvent evaporation technique commonly known in the art.

Polymer composition, drug loading and particle size distribution are significant parameters to select based on clinical needs. In some embodiments, the nanoparticles have an average size of about 0.1 nm to about 5 µm, about 1 nm to about 1 µm, about 10 nm to about 1 µm, about 50 nm to about 1 µm, about 100 nm to about 1 µm, about 250 nm to about 900 nm, or about 600 nm to about 800 nm. In some embodiments, the sizes of the nanoparticles have an average diameter in the range of 50-500 nm. In one embodiment, the nanoparticles have an average diameter of around 100-200 nm. In some embodiments, the tissue stabilization agent embedded in the nanoparticles can be in the range of about 0.05-99, 0.1-95, 0.5-90, 1.0-80, 2.5-70, 5-60, 7-50, 10-40 or 20-30 weight percent to the nanoparticle. In some embodiment, the tissue stabilization agent is in the range of about 0.05 to 50 weight percent to the nanoparticle. A person of ordinary skill in the art will recognize that additional ranges of concentrations and particle sizes within these explicit ranges are contemplated and are within the present disclosure.

In some embodiment, it may be advantageous to use tissue stabilization agent itself as delivery vehicle. For example, PGG formulations have been shown to form a gel under certain conditions. The conditions, such as concentration of PGG and pH during formation of the gel influence the resulting gel properties. In some embodiments, the PGG gel can be formulated to dissolve around 37° C., the body temperature of a patient. Additionally or alternatively, PGG can be formulated as a gel that remains its gel form at around 37° C. or higher temperatures. The gel form PGG can be used as drug delivery vehicle, for example, a slow release delivery vehicle for collagen stabilization agent, with properties adjusted as desired. Thus, the PGG would be both a delivery vehicle and a stabilization agent. The gel form of PGG can also be used in combination with other delivery vehicles such as hydrogel and/or poly(lactic-co-glycolic acid) (PLGA) nanoparticles to provide release profiles for short or extended period for a stabilization agent.

Different approaches for PGG delivery are developed in the discussion herein as well as related general approaches. Collagen stabilization agent such as glutaraldehyde (Glu) can likewise be incorporated alone or in combination with elastin stabilization agent such as PGG. For example, treatment of heart tissue can use: (1) hydrogels, such as Pluronic™ gel comprising a tissue stabilizing agent, such as PGG and/or Glu; (2) tissue stabilizing agent loaded polymeric nanoparticles: PGG alone, Glu alone, or PGG+Glu in the same or different nanoparticles; (3) hydro gel comprising polymeric nanoparticles of (2); and (4) Pluronic™ gel comprising PGG and/or Glu and further comprising polymeric nanoparticles of (2) or the like to form therapeutic compositions with desired controlled release profile.

In some embodiments, the therapeutic composition with a gelling delivery vehicle can be applied directly to the heart tissue, which would gel around the tissue. The mechanical properties of the therapeutic composition upon gelling around the heart tissue can be adjusted so the gelled therapeutic composition stays around the tissue without diffusing into the surrounding tissue that are not of treatment choice. Non-invasively delivery method such as laparoscopy can be employed to deliver the composition.

Treatment with a tissue stabilizing agent can be combined with mechanical stabilization. For example, a wrap can be placed over the exterior of the heart tissue to provide mechanical stabilization along with the chemical stabilization. For example, the therapeutic compositions can be coated along the interior of the wrap and/or embedded in the material of the wrap. The wrap provides a close contact to the heart tissue for consistent drug release in addition to the delivery vehicle described herein. In these embodiments, the wrap additionally physically strengthens the heart tissue to facilitate the normal heart pumping actions. The stabilization agents act to stabilize and strengthen the heart tissue along with inhibiting further dilation of the tissue at the location. The delivery vehicle modulates the release rate of the tissue stabilizing agent within the therapeutic composition. The wrap can be formed from biocompatible polymers, such as polyesters, that can be formed into woven or non-woven fabrics. Alternatively, the wrap can be formed from bioresorbable material such as those disclosed in U.S. Pat. No. 6,258,122 to Tweden et al. entitled "Bioresorbable annuloplasty prosthesis", incorporate herein by reference. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particular, polylactic acid, polyglycolic acid, and copolymers and mixtures thereof.

The site of treatment may need to be aspirated first to alleviate pressure and followed by the delivery of a therapeutic composition containing the tissue stabilization agents. In some embodiments, direct application of the therapeutic composition to the heart tissue can be combined with less invasive procedures treatment, such as using laparoscopic procedure, to deliver the therapeutic composition, optionally using the wrap described above.

In some embodiments, using the delivery device described herein, an effective amount of collagen stabilization agent, such as glutaraldehyde, can be delivered to the heart tissue after the initial fluid aspiration. The collagen stabilization agent can be allowed to interact with the heart tissue for a period of time before being aspirated out. The time period can be for example, about 1 minute to about 1 hour, in further embodiments about 5 min to about 30 minutes, and in additional embodiments about 10 to about 25 mins, and can be longer in some embodiments. A person of ordinary skill in the art will recognize that additional ranges of time within the explicit ranges above are contemplated and are within the present disclosure. Optionally, the collagen stabilization agent treated aneurysm tissue can be rinse with a buffer such as saline before further treatment using another quantity of the same therapeutic composition or another therapeutic composition described herein. The delivery device employed can have multiple ports connected to multiple reservoirs. Alternatively or additionally, the delivery device can be maintained in the vessel while the content of the flow devices is switched. After the initial treatment with collagen stabilization agent, an elastin stabilization agent such as PGG can be delivered for example with block copolymer described herein to heart tissue. Once reaching the heart tissue, the block copolymers forms hydrogel in situ, locking the PGG inside the hydrogel for sustained release. The hydrogel optionally can have nanoparticles encapsulating PGG for longer release. Alternatively, nanoparticles encapsulating PGG without hydrogel can be administered as a dispersion. The solution in the dispersion can optionally have PGG and/or glutaraldehyde.

For appropriate embodiments, a collagen stabilization agent treatment step and an elastin stabilization agent treatment step can be performed sequentially without withdrawal of the delivery device or can be performed as separate steps with withdrawal of the delivery device in between. Based on the condition of the heart, the treatments steps can be performed multiple times with different combination of therapeutic compositions and time intervals. Sometimes the treatment steps can be repeated periodically or when the sustained release of the tissue stabilization agent is significantly diminished. Appropriate diagnostic method can be used to help determine the dose and duration of treatment.

Less Invasive Delivery Device

In general, a device for the delivery of a therapeutic agent comprises a reservoir of the therapeutic agent and structural elements to guide the delivery of the therapeutic agent. For the delivery of the therapeutic gent into a patient's abdominal cavity, the device can provide an appropriate level of control of the delivery process, such as an appropriate nozzle to provide a directed flow. For less invasive procedures, the delivery elements of the device can comprise a catheter type structure operably connected to the reservoir that can be guided to a delivery location after insertion through a small incision. An appropriate control device can be used to control flow from the reservoir into the catheter or other corresponding delivery structure. The tip of the delivery structure can be designed to improve the control of the delivery, such as with a focused opening and/or shields to deflect the flow.

The stabilization composition can be delivered to the heart tissue using a catheter structure. The catheter is configured to access the heart tissue from the exterior of the chest. In some embodiments, the catheter can be used as a channel for the delivery of an applicator, which extends through the catheter channel to deliver the stabilization compositions described herein to the heart tissue. Exemplary applicators include, for example, those disclosed in U.S. Pat. No. 6,494,896 to D'Alessio et al. entitled "Applicator for Laparoscopic or Endoscopic Surgery" and U.S. Pat. No. 5,415,631 to Churinetz et al. entitled "Endoscopic Material Delivery Device", both are incorporate herein by reference. Additionally or alternatively, the stabilization of the heart tissue can be performed through the access of the heart using an access port or alike. An embodiment of an access port is described, for example, in U.S. Pat. No. 5,391,156 to Hildwein et al. entitled "Flexible Endoscopic Surgical Port", in corporate herein by reference.

Figure 3A:
FIG. 3A is an enlarged side view of the tip portion of the catheter of FIG. 2 that maintains the diameter of the catheter.
Figure 3B:
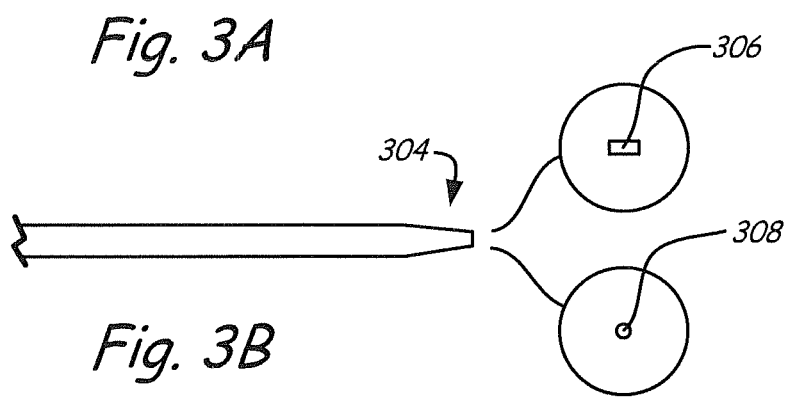
FIG. 3B shows enlarged side and distal end views of the tip portion of the catheter of FIG. 2 with a first tapered configuration with an end view showing a taper to a small circular opening shown in one balloon and a second tapered configuration with an end view having a tapered slit shown in a second balloon.
Figure 3C:
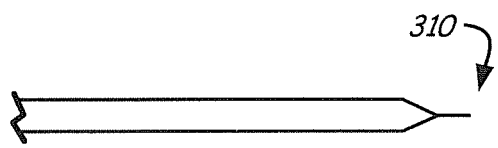
FIG. 3C is an enlarged side view of the tip portion of the catheter of FIG. 2 with a needle like configuration.
Figure 3D:
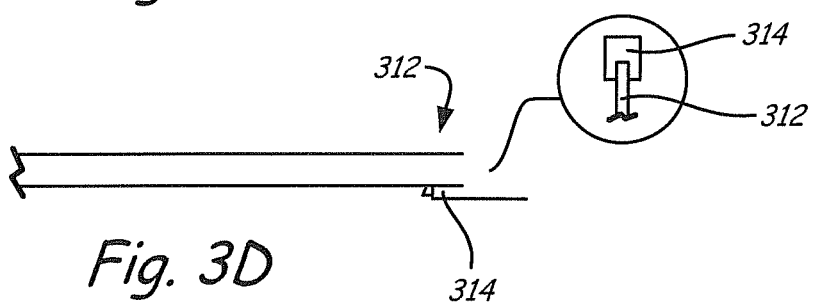
FIG. 3D shows enlarged side and top views of the tip portion of the catheter of FIG. 2 with a directional shield with a top view of the shield shown in the balloon.

Referring to FIG. 2, a device 200 for delivery of the therapeutic composition is shown. A catheter 202 is connected to a reservoir 204 with an optional pump 206 between the catheter and the reservoir. The catheter comprises a distal tip portion 208 that can adopt various configurations to suit different application needs. Four tip portion configurations are illustrated in FIGS. 3A-3D. FIG. 3A is a side sectional view of one embodiment of the catheter showing a tip portion 302 of the catheter that maintained the overall general diameter of the body of the catheter. FIG. 3B is a side sectional view of another embodiment of the catheter showing a tip portion 304 of the catheter that is tapered in diameter with additional variations of the distal opening of the catheter shown in end views 306 and 308. The end view 306 illustrates a distal opening with a rectangular configuration and the end view 308 illustrates a distal opening with a round configuration. FIG. 3C is a side sectional view of yet another embodiment of the catheter showing a tip portion 310 of the catheter that is needle like. The needle like catheter can be used for direct access of heart tissue such as the pericardial cavity. FIG. 3D is a side sectional view of a fourth embodiment of the catheter showing a tip portion 312 of the catheter that comprises a directional shield 314. A top view of the tip portion 312 is additionally shown providing additional prospective of the relationship between the tip portion 312 and the shield 314. The directional shield 314 can protect surrounding elements of the heart tissue in treatment such as blood vessel from the treatment compositions.

In some embodiments, directional catheters and/or one way shields can be used to protect coronary arteries when the stabilization composition is delivery to the heart tissue. In particular, the tip of the applicator can be shaped to provide desired control of the delivery of a stabilization composition. In addition, the pericardium can be bound to the heart muscle at selected locations to form a protective layer over the coronary arteries to protect them from the treatment fluid. The location of the lines of attachment can be selected based on the direction of the delivery of the treatment fluid. For example, the pericardium can be connected to the heart muscle using an ablation tool. The locations of connection could be similar to natural points of connection between the pericardium and the heart muscle referred to as pericardial reflections. A suitable ablation tool is described in U.S. Pat. No. 7,422,588 to Mulier et al., entitled "Pen-Type Electrosurgical Instrument," incorporated herein by reference.

The stabilization composition can also be applied to the heart tissue through a cardiac reinforcement wrap. For example, the stabilization composition can be applied to synthetic material or biological material that is then applied to the patient's pericardium or surface of the heart muscle. The wrap can be secured with suture or other suitable fastener. The stabilization composition can also be used in conjunction with surgical intervention such as those described in the '601 patent by applying the composition after the surgery to stabilized the heart tissues. Access ports, heart tissue manipulating instruments, and soft tissue retractor such as those used in the '601 patent can similarly be used when applying the stabilization composition.

Treatment Procedure

The treatment of the heart tissue with the therapeutic compositions described herein generally involves the effectively direct delivery of the therapeutic composition to the heart tissue in vivo. The delivery of the therapeutic composition can generally be accomplished using a suitable device for a less invasive procedure as described above. The corresponding procedure can be performed with the patient correspondingly prepared for such a less invasive procedure. The therapeutic composition can be delivered in a flowable form so that a catheter or the like can be suitably positioned for the delivery of the therapeutic agent. However, the delivery process can be appropriately controlled since the therapeutic composition can have less than desirable results if the therapeutic fluid contacted other tissue or organs. In additional or alternative embodiments, the therapeutic composition can be delivered in association with a patch or the like. Thus, the procedure can involve the controlled delivery of the therapeutic composition such that the therapeutic composition is delivered to selected locations of the heart tissue.

By binding to and crosslinking collagen in a collagen containing tissue, glutaraldehyde increases the mechanical strength of the tissue. The in vivo application of the glutaraldehyde alone and in combination with PGG have been briefly discussed in the '543 patent and the '605 application with respect to stabilization of connective tissue. For heart tissue treatment the amount of glutaraldehyde, treatment concentration, treatment time, and application of toxicity control agent(s) can be selected to achieve desired treatment effects while avoiding undesirable effects from excessive treatment, such as excessive cellular toxicity and over-stiffening of the heart tissue. Similarly, an elastin stabilization composition can be effective to stabilize the elastin within the tissue to also stiffen the tissue to some degree. The treatment conditions can be adjusted appropriately comparably to a treatment with a collagen stabilization composition.

In general, heart tissue targeted with the therapeutic agent(s) or composition(s) can be stabilized in vivo so as to be less susceptible to protein degradation as well as having improved mechanical strength to resist distortion of the natural shape. For example, by increasing the mechanical strength and/or stiffness of the myocardium, especially at or near the left ventricle, the heart would be expected to increase in size less during the filling of the left ventricle with blood. Also, as the left ventricle contracts, the heart should be more effective at circulating the blood if the heart has expanded less during filling and pressure in the chamber should be greater, which would also correlate with improved pumping function. Similarly, the pericardium functions as a supportive sack surrounding the heart. The pericardium is somewhat elastic so that the sack expands and contracts with the heart. If the pericardium is stiffened and/or corresponding mechanically strengthened through treatment with a therapeutic agent, the constraining effect of the pericardium can act similarly to the increasing of the mechanical strength of the heart muscle itself. Treatment of the pericardium can be effective and relatively straightforward since the pericardium surrounds the heart, which blocks direct access to the heart muscle. As noted above, different layers or combinations thereof of the pericardium can be treated with the therapeutic compositions. For example, the therapeutic composition can be applied to the outer surface of the pericardium, to the visceral pericardium and/or delivered into the volume generally occupied with the pericardial fluid.

In general, the heart can be surgically accessed through an appropriate opening into the chest of the patient. However, less invasive procedures provide an appropriate level of access for the delivery of treatment compositions to selected locations while providing less disruption of the patient's tissues so that the recovery time for the patient can be correspondingly reduced. In appropriate less invasive procedures, a small incision is made in the patient's chest to provide access to the chest cavity. Appropriate tools can be used to provide a path to the pericardium and/or heart muscle. Multiple small incisions can be made to provide further ability to manipulate the devices and/or simultaneous use of a plurality of devices as well as to optionally provide visualization, such as with a thoracoscope. If desired, ports can be placed at the incision sites to stabilize the site. To provide access to the heart, one or both of the patient's lungs can be partially collapsed. In some embodiments, the pericardium is cut away to provide access to the heart muscle for the application of therapeutic compositions. Additionally or alternatively, the therapeutic composition can be applied to the surface of the pericardium. Also, as noted above, in some embodiments the therapeutic composition can be delivered into the space holding the pericardial fluid, with or without removing the fluid.

Figure 4:
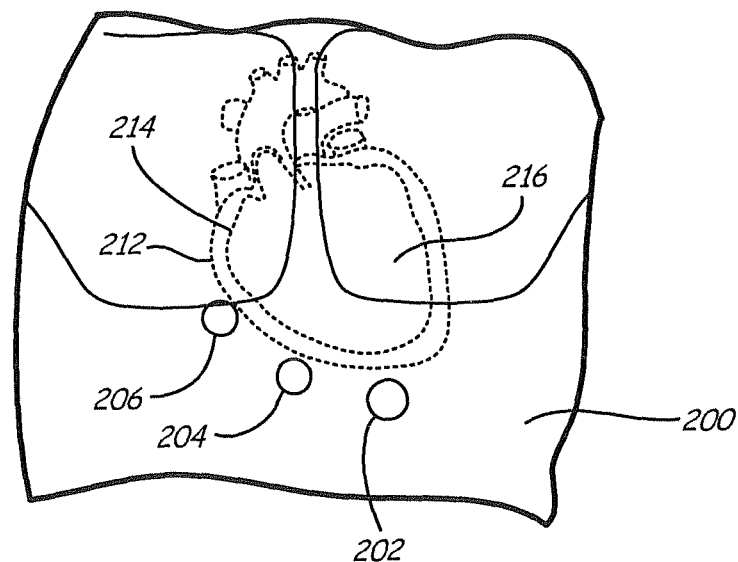
FIG. 4 is a schematic diagram of a patient's chest with three access ports to the heart.
Figure 5:
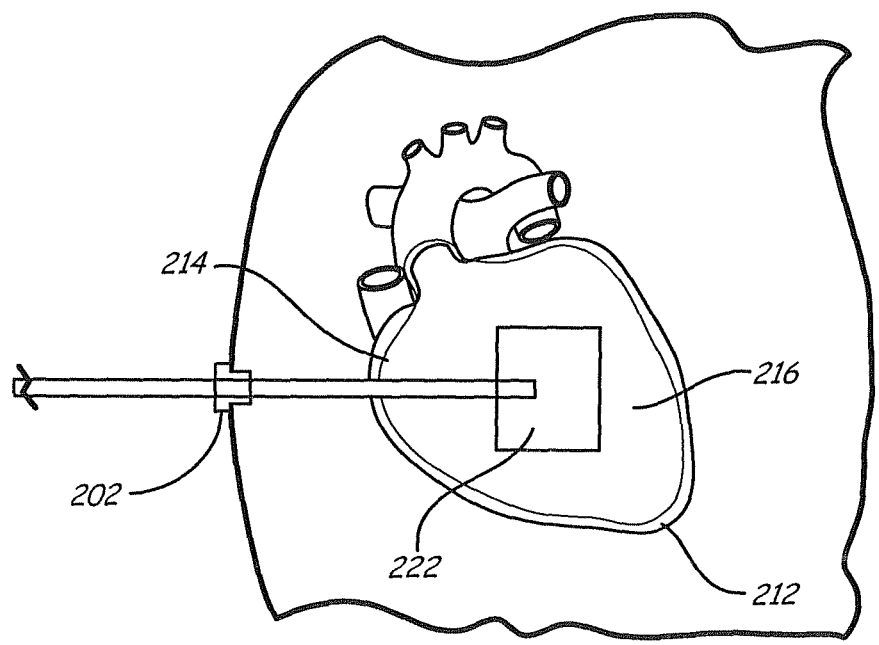
FIG. 5 is a side sectional view of FIG. 4 with a catheter delivered through one of the ports.

Referring to FIG. 4, a patient's chest 200 is shown with three ports 202, 204, 206. Ports 202, 204, 206 can provide access to pericardium 212 and/or heart 214, especially in the vicinity of left ventricle 216. Referring to a sectional side view in FIG. 5, a catheter or cannula 220 is shown extending through port 202 to reach heart tissue at or near left ventricle 216. To reach the heart muscle, the location can have been prepared by cutting through pericardium 212 to expose the heart muscle. Alternatively, or additionally, catheter/cannula 220 can be directed to the surface of pericardium 212 to deposit therapeutic composition along the surface of the pericardium. Catheter 220 can have a needle or the like at its distal tip to inject a therapeutic composition into the pericardium, such as in the volume naturally occupied by the pericardial fluid. In an alternative embodiment, the therapeutic composition can be delivered with a patch or the like 222 that can be applied to the surface of the pericardium or the heart.

As noted above, it can be desirable to control the delivery of the therapeutic composition. If the therapeutic composition reacts quickly or if the therapeutic composition is absorbed into the tissue, then the therapeutic composition can be delivered as a fluid at the selected positions, such as at or near the left ventricle. If the therapeutic composition reacts slowly or if the therapeutic composition can flow off of the tissue where applied, the therapeutic composition can be applied with a delivery vehicle, such as a hydrogel or other polymer composition, that can hold the therapeutic composition at the delivery site while the therapeutic composition stabilizes the tissue over time through elution from the delivery vehicle. Similarly, a patch or the like can be used to deliver the therapeutic composition at a fixed location such that the therapeutic composition can again elute from the patch.

In some embodiments, a collagen crosslinking/stabilization agent can be administered alone, or an elastin stabilization agent can be delivered alone. In other embodiments, the collagen crosslinking/stabilization agents can be combined with elastin stabilization agent. In yet other embodiments, the collagen crosslinking/stabilization agent and elastin stabilization agent can be administered in separate application steps sequentially to the tissue with optional rinse steps in between. The collagen crosslinking/stabilization agent and elastin stabilization agent can each have an appropriate application time, composition, delivery vehicle, and concentration. The treatment parameters such as concentration, composition, delivery vehicle, application device and method of delivery can be adjusted to suit variety of needs with respect to stabilizing tissues with collagen and/or elastin component.

Ben-Horin et al. studied in Am J Med. 2005, 118 (6):636-40, entitled "The composition of normal pericardial fluid and its implications for diagnosing pericardial effusions," incorporated herein by reference, the composition of pericardial fluid in patients undergoing open heart surgery. They found that the fluid is made up of a high concentration of lactate dehydrogenase (LDH), protein and lymphocytes. In a healthy individual there is usually 15-50 ml of clear, straw-colored fluid. The pericardial fluid may be withdrawn prior to the treatment. Once the pericardial cavity is flushed with single or multiple applications of the treatment composition, the pericardial fluid can be replenished after the treatment to restore the proper heart function. In some embodiments directed to the delivery of the therapeutic composition within the volume occupied by the pericardial fluid, each application of the treatment composition may be performed for no more than about 2 hours, in further embodiments no than 1 hour, in additional embodiments from about 1 minute to about 30 minutes. Person of ordinary skill in the art will recognize that additional ranges of time within the explicit ranges of time are contemplated and are within the present disclosure.

The embodiments above are intended to be illustrative and not limiting. Additional embodiments are within the inventive concepts. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. All patents, patent applications, and publications referenced herein are hereby incorporated by reference herein to the extent that the incorporated material is not contrary to any of the explicit disclosure herein.

What is claimed is:

1. A method for the stabilization of heart tissue in a living subject, the method comprising
applying a therapeutic composition to the pericardium of the living subject, to the outer surface of the myocardium of the living subject, or a combination thereof,
wherein the therapeutic composition comprises an elastin stabilization agent, a collagen stabilization agent, or a combination thereof, wherein the elastin stabilization agent comprises a compound that comprises at least one phenolic hydroxyl group bound to a hydrophobic core and wherein the collagen stabilization agent comprises a photo-activated crosslinking agent, or an aldehyde with at least two aldehyde groups, a polyamine with carbodiimide, a photo-catalytic dye, genipin, an epoxide, an azide ester, or a combination thereof.

2. The method of claim 1 wherein the therapeutic composition further comprises a delivery vehicle.

3. The method of claim 2 wherein the delivery vehicle comprises precursor of hydrogel, polymer nanoparticles with the therapeutic composition embedded therein, or a combination thereof.

4. The method of claim 3 wherein the precursor of hydrogel comprises poloxamer block copolymers.

5. The method of claim 3 wherein the nanoparticles comprises poly(lactic acid-co-glycolic) acid.

6. The method of claim 1 wherein the elastin stabilization agent and the collagen stabilization agent are applied simultaneously or sequentially.

7. The method of claim 1 wherein the therapeutic composition is applied through the access of the heart using a catheter structure.

8. The method of claim 1 wherein the therapeutic composition is applied through the access of the heart using an access port or alike.

9. The method of claim 1 wherein the therapeutic composition is applied to the heart tissue using a cardiac reinforcement wrap or a patch.

10. The method of claim 1 further comprising an aspiration step before the application of the therapeutic composition.

11. The method of claim 1 wherein the application of the therapeutic composition is repeated with the same or a different therapeutic composition.

12. The method of claim 1 wherein the elastin stabilization agent comprises a compound that is tannic acid or a derivative thereof, a flavonoid or a flavonoid derivative, a flavolignan or a flavolignan derivative, a phenolic rhizome or a phenolic rhizome derivative, a flavan-3-ol or a flavan-3-ol derivative, an ellagic acid or an ellagic acid derivative, a procyanidin or a procyanidin derivative, anthocyanins, quercetin, (+)-catechin, (−)-epicatechin, pentagalloylglucose, nobotanin, epigallocatechin gallate, gallotannins, an extract of olive oil or a derivative of an extract of olive oil, cocoa bean or a derivative of a cocoa bean, *Camellia* or a derivative of *camellia*, licorice or a derivative of licorice, sea whip or a derivative of sea whip, aloe vera or a derivative of aloe vera, chamomile or a derivative of chamomile, a combination thereof, or a pharmaceutically acceptable salt thereof.

13. The method of claim 1 wherein the elastin stabilization agent comprises pentagalloylglucose, an analog of pentagalloylgiucose, a pharmaceutically acceptable salt thereof, or a combination thereof.

14. The method of claim 1 wherein the collagen stabilization agent comprises an aldehyde with at least two aldehyde groups, a polyamine with carbodiimide, a photo-catalytic dye, genipin, an epoxide, an azide ester, or a combination thereof.

15. The method of claim 1 wherein the collagen stabilization agent comprises glutaraldehyde.

16. The method of claim 1 wherein the collagen stabilization agent comprises a photo-activated crosslinking agent.

* * * * *